United States Patent [19]
Virta et al.

[11] Patent Number: 5,224,140
[45] Date of Patent: Jun. 29, 1993

[54] METHOD AND APPARATUS FOR PANORAMIC RADIOGRAPHY

[75] Inventors: Arto Virta, Helsinki; Pekka Strömmer; Timo Müller, both of Espoo, all of Finland

[73] Assignee: Planmeca Oy, Finland

[21] Appl. No.: 836,788

[22] Filed: Feb. 14, 1992

[30] Foreign Application Priority Data

Feb. 15, 1990 [FI] Finland .................................. 910739

[51] Int. Cl.$^5$ .............................................. A61B 6/14
[52] U.S. Cl. .......................................... 378/38; 378/40
[58] Field of Search .............................. 378/38, 39, 40

[56] References Cited

U.S. PATENT DOCUMENTS

| | | |
|---|---|---|
| 4,599,739 | 7/1986 | Nishikawa . |
| 4,741,007 | 4/1988 | Virta . |
| 4,783,793 | 11/1988 | Virta . |
| 4,833,699 | 5/1989 | Gardner . |

FOREIGN PATENT DOCUMENTS

| | | |
|---|---|---|
| 0062962 | 2/1982 | European Pat. Off. . |
| 0193650 | 12/1985 | European Pat. Off. . |
| 0214486 | 8/1986 | European Pat. Off. . |
| 0215757 | 9/1986 | European Pat. Off. . |
| 0262500 | 9/1987 | European Pat. Off. . |
| 1955294 | 5/1970 | Fed. Rep. of Germany . |
| 2646638 | 4/1978 | Fed. Rep. of Germany . |
| 3513455 | 10/1986 | Fed. Rep. of Germany . |
| 833506 | 2/1985 | Finland . |
| 840044 | 7/1985 | Finland . |
| 861463 | 7/1987 | Finland . |

*Primary Examiner*—Craig E. Church
*Attorney, Agent, or Firm*—Jones & Askew

[57] ABSTRACT

The invention concerns a method and apparatus for narrow-beam tomography in which x-ray radiation is aimed to pass through the object to be radiographed onto a movable ($v_1$) x-ray film (F). The object (P) is kept stationary in a certain position, while the x-ray source and the film cassette (14) are rotated about a vertical virtual axis of rotation (A-A). In the first operating mode for the panoramic radiography of the dental arch the patient (P) is supported by positioning means so that the sharply imaging plane (P-P) is located between the virtual axis of rotation (A-A) of the x-ray beam (X) and the film plane. In the second operating mode for the radiography of transversal projections of the dental arch (L) the patient (P) is supported in such a stationary position that the virtual axis of rotation (A-A) of the x-ray beam (X) is located in the area between the sharply imaging tissue layer (P-P) and the film plane (F). In the second operating mode the film (F) is moved in a direction which is opposite to the film transfer direction in the first operating mode.

13 Claims, 9 Drawing Sheets

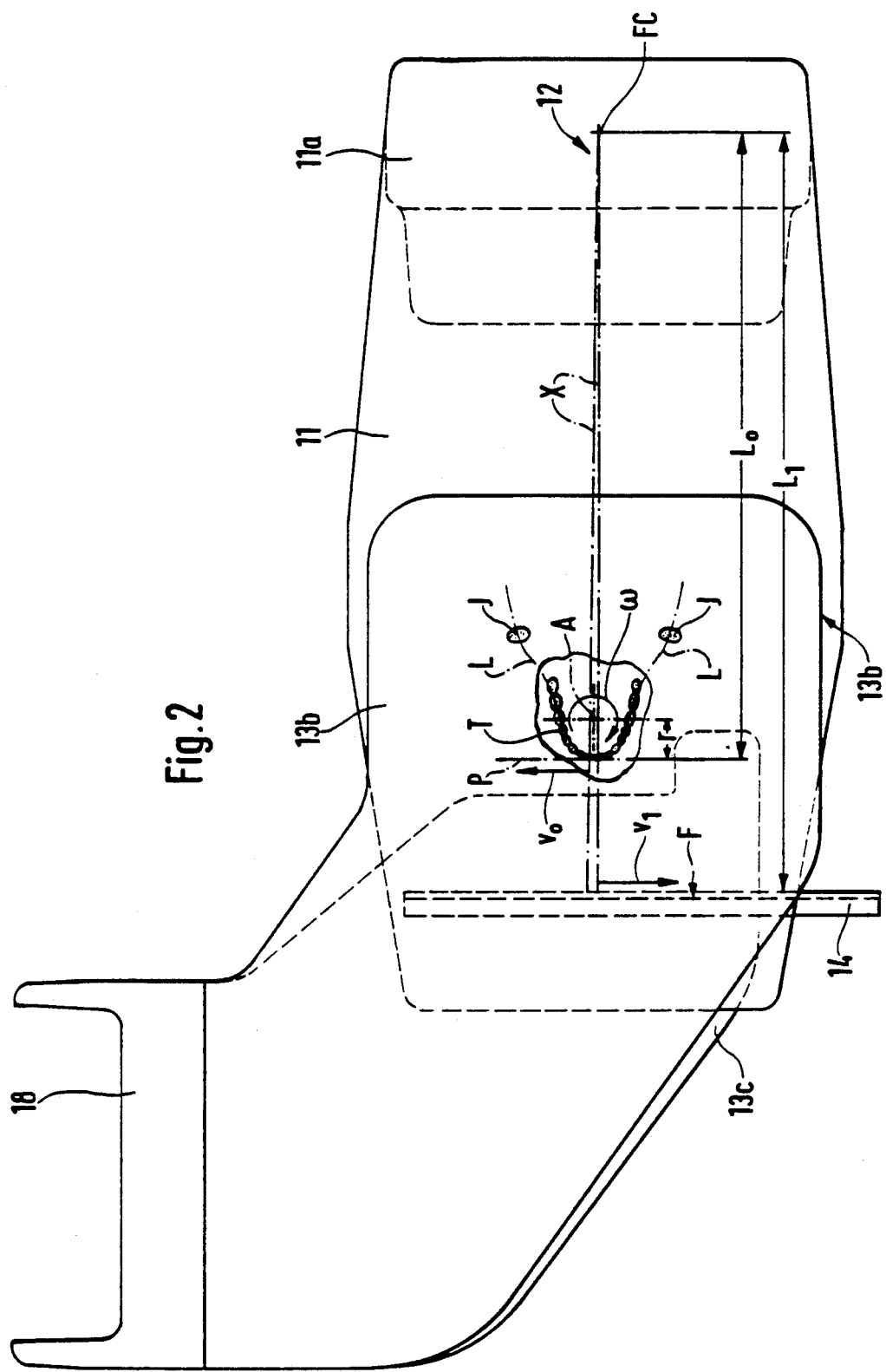

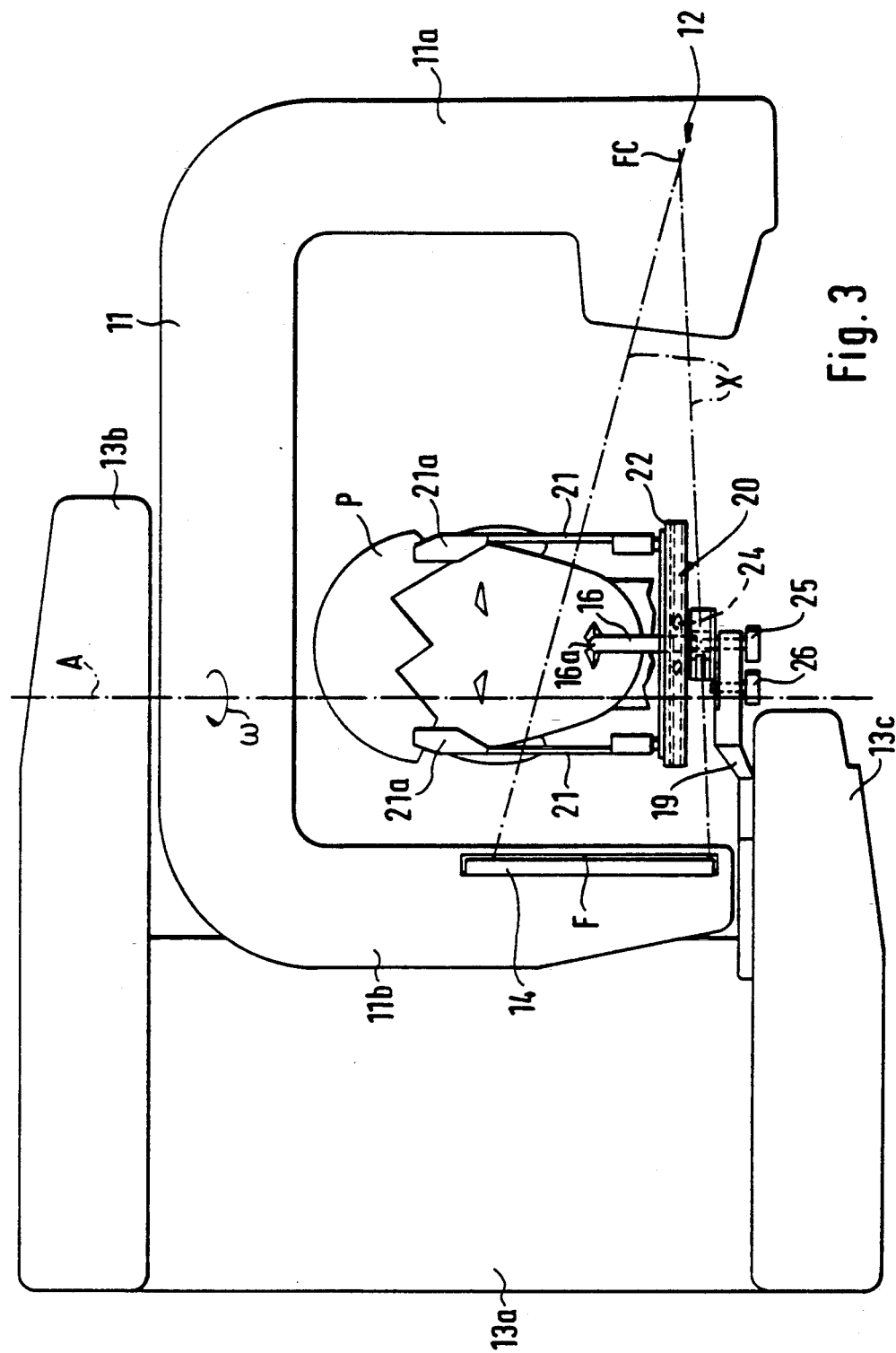

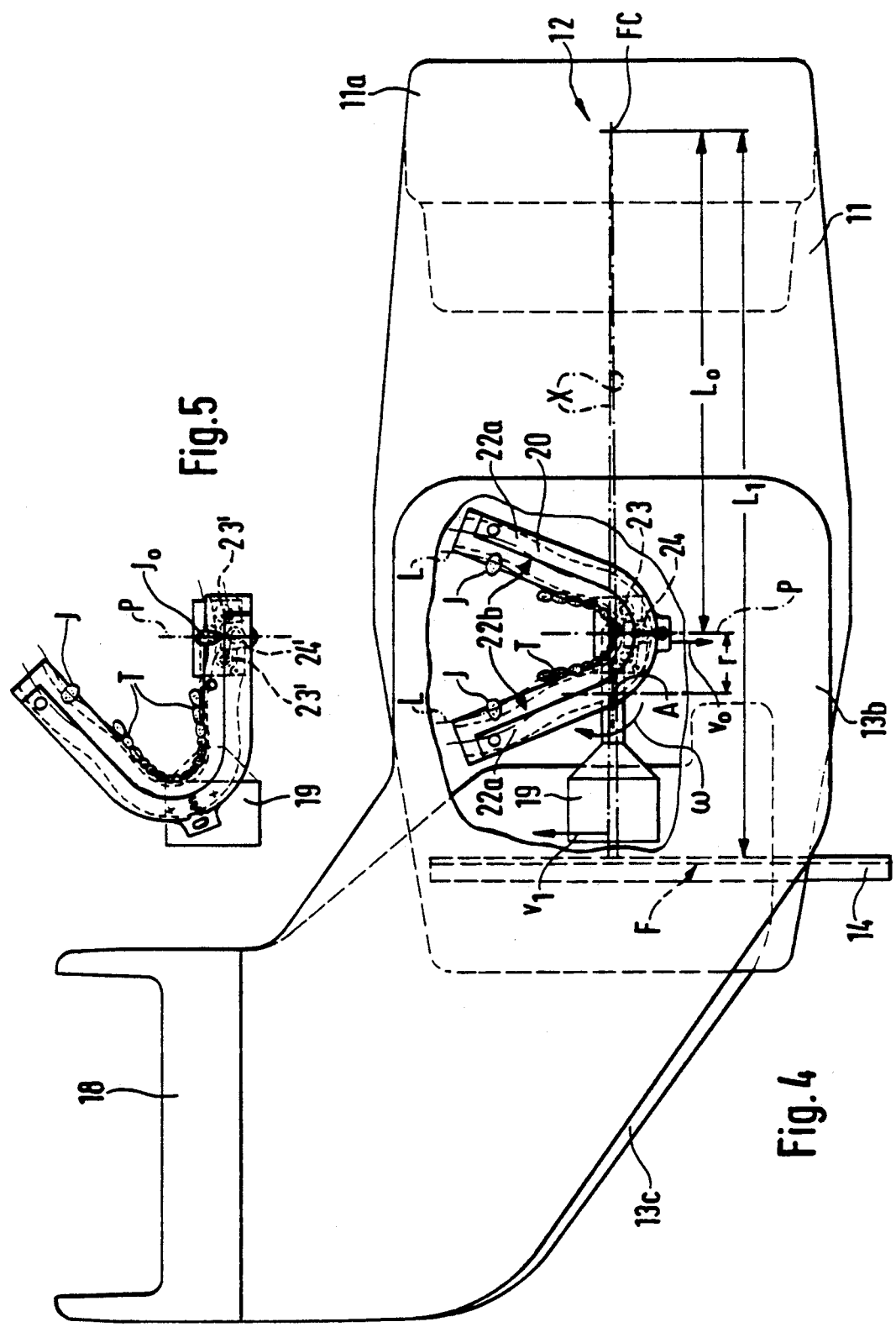

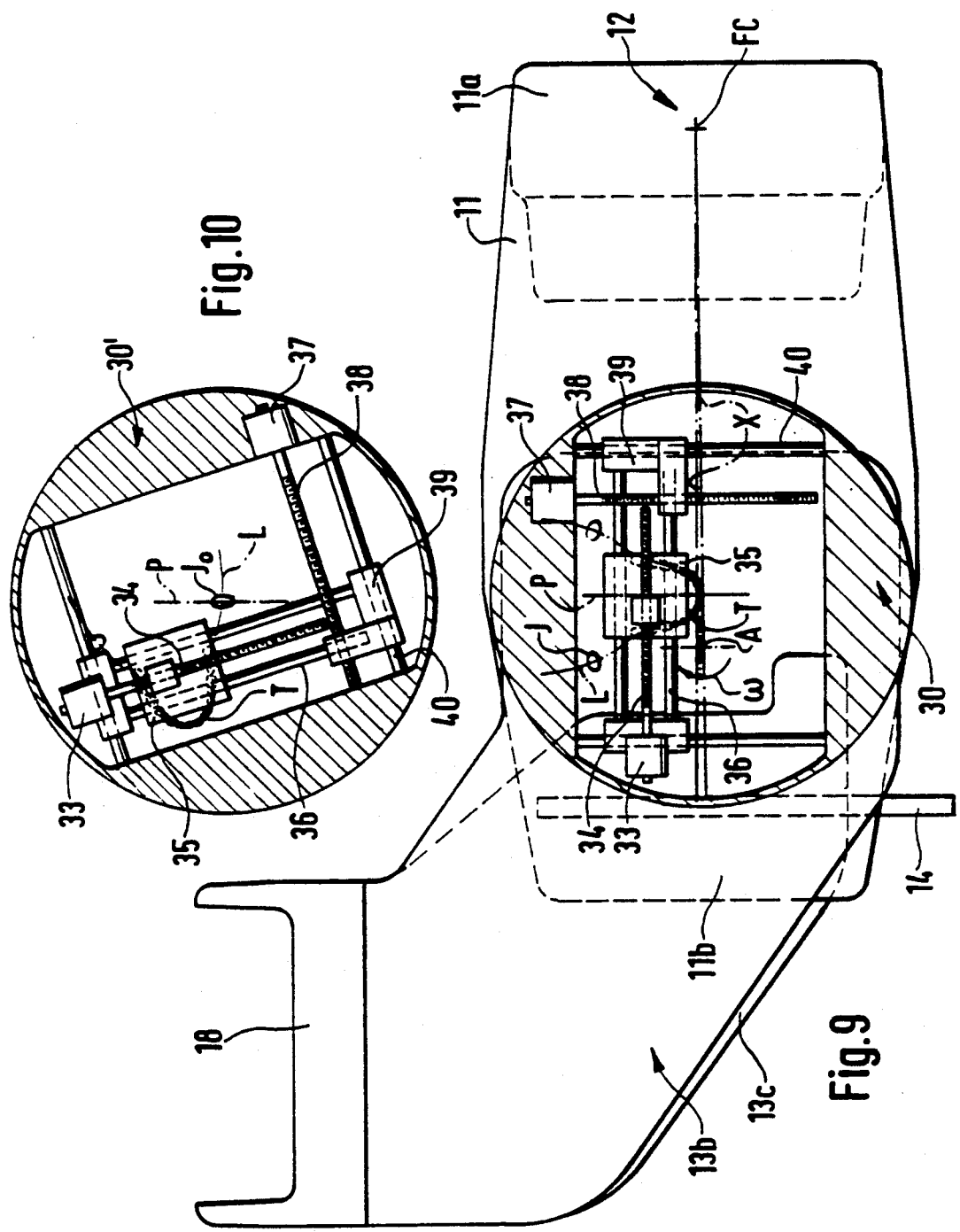

METHOD AND APPARATUS FOR PANORAMIC RADIOGRAPHY

The invention relates to a method applicable to narrow-beam panoramic radiography, in which method the narrow beam of an x-ray source is focused through the object to be radiographed onto a movable x-ray film; in which method the object to be radiographed from the patient is held stationary in a certain position while the x-ray source and the film cassette are simultaneously rotated about a virtual axis of rotation, which is preferably aligned vertical; and in which method according to its first operating mode the patient is supported by positioning means for exposing panoramic radiographic images of the dental arch so that the sharply imaging plane is formed between said virtual axis of rotation of the x-ray beam and the film plane.

Furthermore, the invention concerns a panoramic tomographic apparatus, in particular for dental radiography, said apparatus comprising a first body part to which is pivotally mounted in bearings, preferably rotating about a vertical axis, a second body part, whose one end carries an x-ray tube and the opposite end an x-ray film cassette, capable of holding an x-ray film, and the object to be radiographed from the patient can be located between said x-ray tube and said film cassette, and said apparatus further incorporates an actuator apparatus, capable of rotating said rotatable body part in a plane, preferably horizontally, for exposing a panoramic radiographic image.

Most panoramic radiographic equipment intended for dental radiography are by their function and construction so designed that their x-ray source is rotated about the patient's skull, whereby the dental arch can be imaged onto a movable film in a planar development. In order to achieve a sharp image of the object onto the film with a simultaneous desired "blurring" of the structures situated along the beam axis in the front or rear of the object, the film speed orthogonally to the exposing beam must be equal to the sweep velocity of the beam at the imaged object multiplied by the magnification. The magnification is set by the ratio of distance from the focus point to the film plane to the distance from the focus point to the object being imaged. The thickness of sharply imaging layer is linearly proportional to the distance of the virtual axis of rotation from the film plane and inversely proportional to the magnification and the width of the x-ray beam. Only the mutual locations of the focus point, imaged object and film plane are relevant to the radiographic process. By contrast, the location of the virtual axis of rotation is solely related to the sweep velocity.

A radiographic apparatus intended for dental panoramic tomography has predominantly been used for radiographing the dental arch and the temporo-mandibular joints.

Prior-art panoramic radiographic equipment expose the x-ray image in a plane aligned in parallel coincident with the dental arch. Recently, however, a growing need has arisen for exposing transversal projection images in conjunction with different kinds of dental treatments such as teeth transplant operations. Transversal projection images in this context mean sectional images radiographed in a transversal plane essentially orthogonal to the mandible or the distal end of the dental arch. Presently, transversal projection images can be radiographed only using extremely costly CT scanners or complicated radiographic equipment having special constructions developed further from panoramic radiographic apparatuses, all of these having a price which is several times higher than that of conventional panoramic radiographic apparatuses.

Conventional panoramic tomographic apparatuses for dental radiography are exemplified in FI patent 73091 (corresponding U.S. Pat. No. 4,741,007) and FI patent application 853524 (corresponding U.S. Pat. No. 4,783,793), both filed by the applicant. Hence, the principal purpose of the present patent is to further develop the apparatuses and other similar panoramic tomographic x-ray apparatuses disclosed in the above mentioned patents and the application filed by the applicant so that different transversal radiographic projections become feasible using simple accessories or arrangements without essentially increasing the price of the apparatus.

To make it possible to image a transversal projection with prior-art panoramic radiographic equipment, for example, in the middle of the dental arch at the incisors, the person being radiographed must be placed in the apparatus so that the x-ray beam sweeps in the direction of the projection plane over the object to be radiographed. In prior-art equipment this is not, however, possible principally because the space provided for the patient's head is insufficient and in this exposure position the imaging elements are bound to hit the back of the patient's head during their orbiting. The goal of the present invention is to offer a novel solution to the above discussed problem.

The invention aims to achieve such a narrow-beam tomographic method, in particular for dental radiography, that can be used for radiographing any transversal projection of the dental arch and also a projection at, for instance, the ear channel. Such a method can bring an essential improvement to the operating merit of conventional panoramic tomographic equipment and make an investment in such equipment more profitable and justified in smaller medical care units than before due to the expansion in the applications of the equipment.

To achieve the goals described above and discussed later, the method according to the invention are principally characterized in that, for the radiography of transversal projections of the dental arch according to the second operating mode of the invention, the patient is supported and located in such a position that the virtual axis of rotation of the x-ray beam is located in the area between the sharply imaging tissue layer and the film plane, and the sharply imaging tissue layer is located to the side of the x-ray source focus point with respect to the virtual axis of rotation and that the x-ray film is moved at the velocity determined by the imaging equation toward a direction which is opposite to the film motion direction used in the first operating mode.

Furthermore, the apparatus according to the invention is principally characterized in that the apparatus comprises such positioning and auxiliary elements with which the patient can be supported for the radiography of transversal projections to such a position in which the sharply imaging plane is located in the area between the focus point of the x-ray source and the virtual axis of rotation of the x-ray beam and that the motion of the x-ray film cassette is controlled by the control system of the apparatus to occur in a direction opposite to that of conventional panoramic radiography in which the sharply imaging plane is located in the area between the plane of the x-ray film and the virtual axis of rotation.

The invention is based on the realization that the imaging conditions of narrow-beam tomography are also fulfilled within the so-called back beam area formed between the virtual axis of rotation and the focus point of the x-ray source. Starting from this fact, the invention has achieved the development of a method and an apparatus whose implementation allows the location of the patient for transversal radiography within the frame of an essentially conventional panoramic radiographic apparatus to such an area which provides sufficient space for imaging without the collision hazard of imaging elements, yet permitting desired alignment of the patient in a suitable position.

Since, in accordance with the invention, the layer being imaged is located to the area between the virtual axis of rotation and the focus point of the x-ray source, this correspondingly dictates that the direction of film cassette motion must be reversed with respect to that used in conventional panoramic radiography.

The principles of the invention allow the implementation of a simple and easy-to-use accessory apparatus for conventional panoramic radiographic equipment that facilitates transversal radiography. The accessory apparatus can be adapted for automatic control which is based on data entered in the apparatus. The accessory apparatus can also be designed for rapid and easy attachment to the panoramic radiographic equipment proper and similar detachment and removal from the equipment after exposure.

Also conventional panoramic radiographic equipment already in use can be equipped with the accessory apparatus in accordance with the present invention, thus widening the applications of such equipment. The invention can be implemented in new panoramic radiographic equipment by factory installation of such patient positioning facilities whose functions are sufficiently flexible to allow the alignment of the patient to both the normal panoramic imaging position and the transversal projection imaging position employed in the invention.

The method and apparatus according to the invention facilitates a significantly wider application of conventional panoramic radiographic equipment with relatively low additional investments.

The invention is next examined in greater detail by making reference to the figures of the attached drawing which illustrate diagrammatically a few exemplifying embodiments of the present invention, whereby the illustrating details must not be construed to limit the applications of the invention.

FIG. 2 shows the apparatus illustrated in FIG. 1 in a top view. Additionally shown in FIG. 2 are the essential system parameters related to the imaging geometry and the location of the dental arch.

FIG. 3 shows in a similar view to that of FIG. 1 a panoramic radiographic apparatus equipped with patient positioning elements according to the invention, said elements being adjusted for such a position of the patient in which a transversal projection image can be exposed in a vertical plane which is orthogonal to the dental arch at the incisors.

FIG. 4 shows in a top view similar to that of FIG. 2 the placement of the patient positioning elements and system parameters of imaging geometry in accordance with the invention.

FIG. 5 shows the position of the patient positioning elements and location of the objects to be imaged when the area to be imaged is the vertical transversal projection of the temporomandibular joint.

FIG. 9 shows in a top view the elements as FIG. 8 complemented with marking of system parameters related to the imaging geometry.

FIG. 10 shows the patient support apparatus illustrated in FIGS. 8 and 9 rotated in a position suitable for radiographing a vertical transversal projection at the temporo-mandibular joint.

Figure 1:
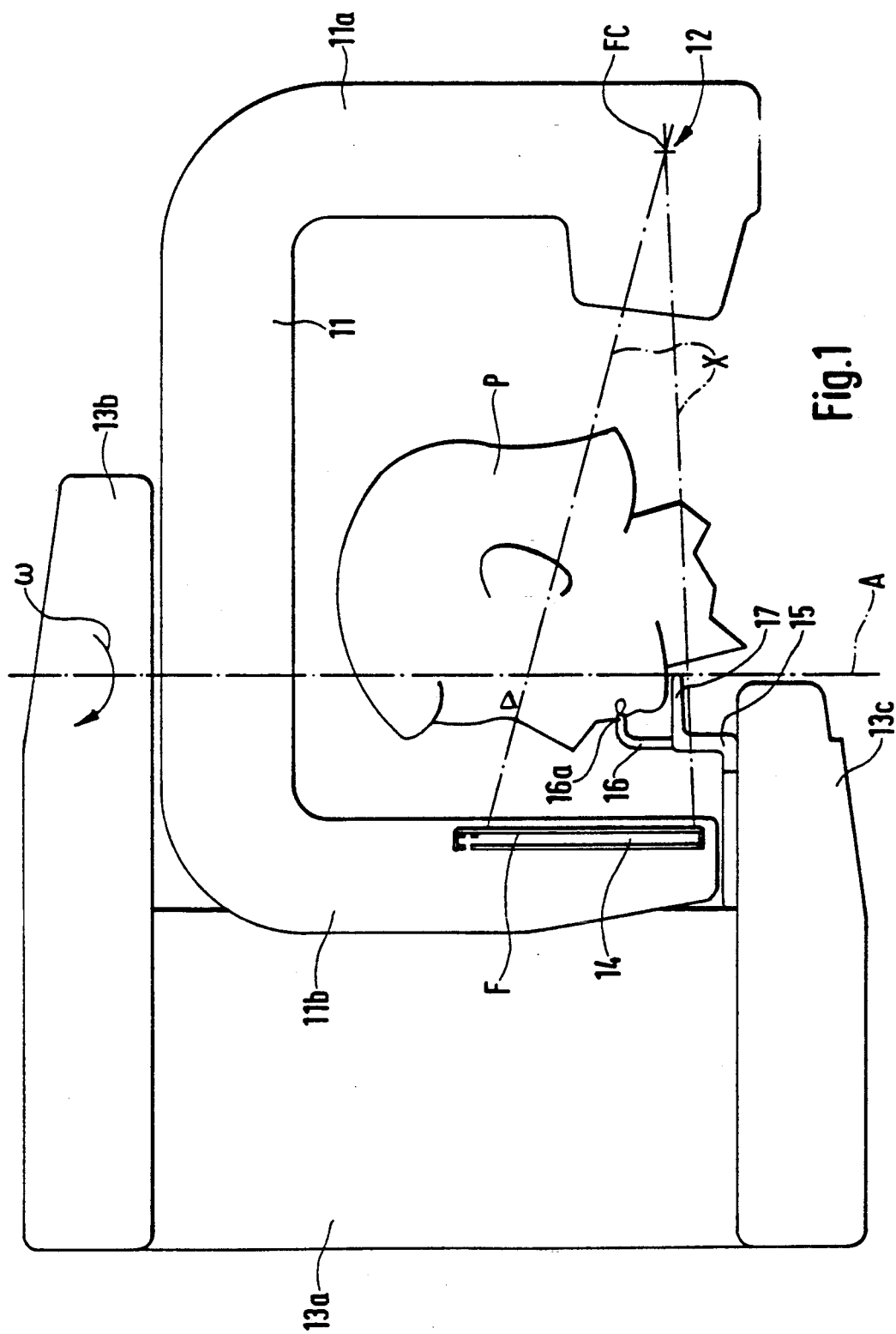
FIG. 1 shows diagrammatically in a side view a conventional panoramic radiographic apparatus of dental radiography with its patient positioning elements.
Figure 6:
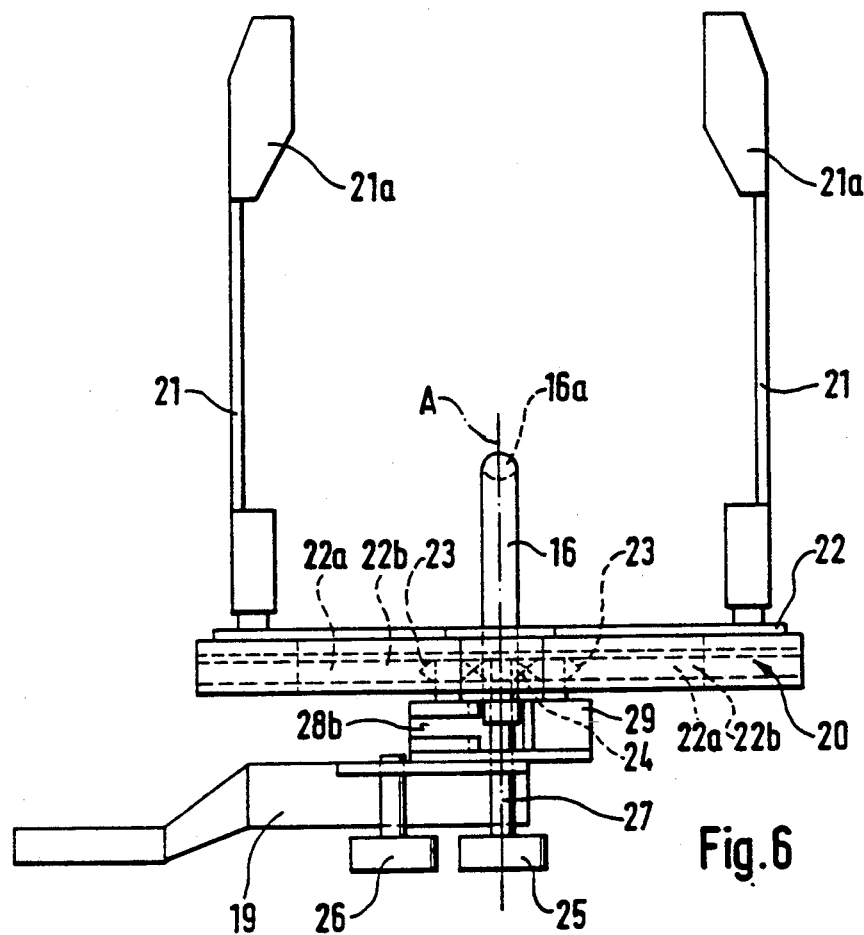
FIG. 6 shows in a front view the patient support elements according to the invention.
Figure 7:
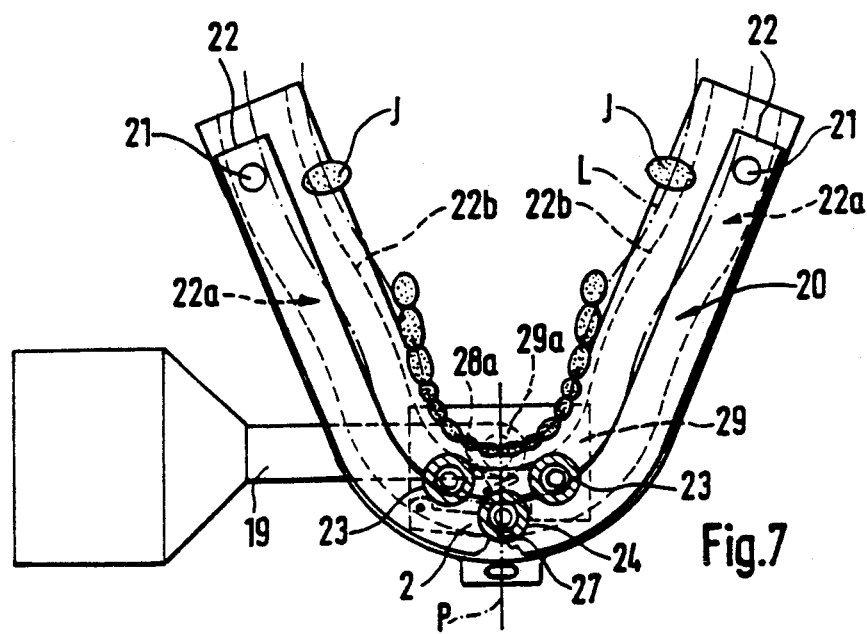
FIG. 7 shows the same items as FIG. 6 but in a top view.
Figure 6A:
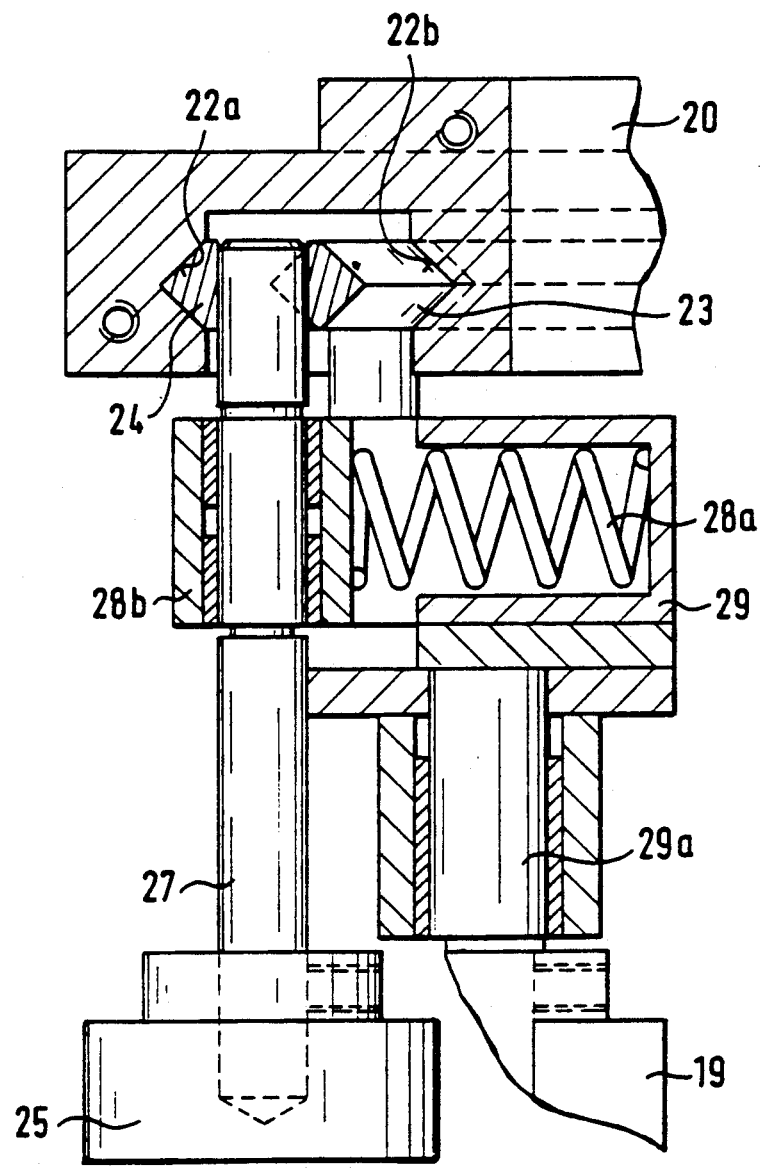
FIG. 6A shows the elements of FIG. 6 in a vertical section along line A-A marked in the diagram.

According to FIGS. 1 and 2, the principal elements of a conventional panoramic radiographic apparatus based on narrow-beam tomography comprise a so-called C-arm incorporating a horizontal part 11 plus vertical parts 11a and 11b between which the patient P to be radiographed is placed. One vertical part 11a of the C-arm supports an x-ray source 12, while the other vertical part 11b carries an x-ray film cassette 14. The cassette 14 contains a film F onto which the panoramic image of the patient's dental structure is exposed. The film cassette 14 with its contained film F is arranged to be movable by means of a conventional motor actuator (not shown) simultaneously with the rotational motion of the C-arm about a nonstationary vertical axis A-A at an angular velocity $\omega$. During the exposure, the radiation is emitted from a focus point FC of the x-ray source 12 as a narrow beam X as illustrated in the horizontal section of FIG. 2. In FIGS. 1 and 2 the dental arch is designated with reference L, the dental arch with reference T and the sections of the temporo-mandibular joints with reference J. According to FIG. 2, the instantaneous imaging takes place in the plane P-P as described by the basic formula of panoramic radiography given below:

$$v_1/v_0 = L_1/L_0$$

$$v_0 = \omega \cdot r,$$

where $L_0$ = distance from the focus point F to the instantaneously imaged point of the layer being imaged $L_1$ = distance from the focus point F to the film plane $\omega$ = angular velocity of rotational motion about the virtual axis of rotation $r$ = distance of imaged point from the virtual axis of rotation of the rotational motion $v_1$ = velocity of image point on the image or film plane.

As evident from FIGS. 1 and 2, the imaging plane P-P is in conventional panoramic radiography located between the virtual axis of rotation A and the plane of the film F. In conventional radiographic equipment, the virtual axis of rotation A is at point A-A during the exposure of the front part of the dental arch, after which it moves in the manner described in, for example, the FI patent 73091 (corresponding U.S. Pat. No. 4,741,007) filed by the applicant.

FIG. 1 shows the members with which the patient P is supported in the area remaining within the C-arm during the conventional front-beam radiography in which the imaging plane P-P is located between the film plane F and the virtual axis of rotation A-A. These support members include a frame part 15 which is removably attached to a horizontal beam 13c of the radiographic equipment. The frame part 15 carries a jaw support 17 and an extension 16, whose distal end is provided with a supporting bitestick 16a that the patient places in between his/her incisors and bites firmly. The C-arm 11,11a,11b is rotatably mounted in bearings on a horizontal part 13b of the frame part 13a. The frame part 13a is arranged vertically movable by means of the member 18 along the vertical column (not shown) of the apparatus that on its turn is supported by the pedestal structures (not shown).

The patient P is preferably placed in the apparatus in a standing position and the C-arm 11 is adjusted to proper elevation according to the patient's height by moving the arm along the vertical beam of the frame part 13a. When necessary the patient can support him/herself by handles (not shown). The apparatus can also be implemented in such a manner that the patient can sit in a chair whose height and position are arranged adjustable.

In the following, making reference to FIGS. 3, 4 and 5, are described the principles along which the patient P is supported according to the invention during transversal projection radiography. In FIGS. 3 and 4 the standard support elements 15,16,16a,17 of a conventional panoramic radiographic equipment are replaced by specially designed patient support elements 20 according to the invention that allow the rapid location of the patient P within the C-arm in a predetermined position which is safe from the collision risk of the imaging elements 11b,14. FIG. 4 shows the radiography of the transversal projection of the dental arch L at the incisors in the vertical plane P-P. The invention is hereby characterized in that imaged plane P-P is located to the side of the focus point FC of the x-ray beam X with respect to the virtual axis of rotation A, instead of being located to the side of the film F as is the case in conventional panoramic radiography (FIGS. 1 and 2), which means that the virtual axis of rotation A, about which the x-ray beam X is rotated, is located according to the invention between the imaging plane P-P and the plane of the film F. Using the same designations as in FIG. 4, the imaging formula is identical to that valid for conventional panoramic radiography, that is:

$$v_1/v_0 = L_1/L_0$$

where $$v_0 = \omega \cdot r$$

where $L_1$ = distance from the focus point (FC) to the film plane (F)

$L_0$ = distance from the focus point (FC) to the sharply imaging layer (P-P)

$\omega$ = angular velocity of rotational motion about the virtual axis of rotation A-A $r$ = distance of imaged plane P-P from the virtual axis of rotation A.

It must be noted that transfer direction (at velocity $v_1$) of the film F and the film cassette 14 are according to the invention opposite to that used in conventional panoramic radiography (FIGS. 1 and 2).

FIGS. 3 ... 7 show the first set of members and elements according to the invention with which the patient P can be supported during the exposure of transversal projection images. These means comprise a support arm 19, whose elements allow the connection of the patient positioning members with quickconnects to the horizontal beam 13c of the frame part, and correspondingly, the detachment of said members. During the exposure of transversal projection images, the accessory means illustrated in FIGS. 3 ... 7 are mounted to replace those patient positioning means 15,16,16a,17 shown in FIG. 1.

The patient positioning and supporting means illustrated in FIGS. 3 ... 7 comprise vertical support members 21 which have temporal support pads 21a at their upper ends. The vertical support members 21 are pivotally attached at their lower ends to the rear ends of rotating arms 22, which are pivotally mounted on hinges at their front ends to the support part 20 so as to be horizontally rotatable, whereby the support members 21 can be opened and rotated aside to place the patient P to be backed by the support part 20. The support part 20 is shaped essentially conforming to the dental arch. The support part 20 itself is mounted to the support arm 19 by means of V-bevelled support wheels 23 and 24 running in correspondingly V-notched guide grooves 22a and 22b machined to the inside of the support part 20.

The support wheels 23 are arranged rotatable in bearings on an intermediate frame 29, which is attached by a vertical pivotally mounted shaft 29a to the support arm 19. The third support wheel 24, which rolls along the outer guide groove 22a of the support part 20, is rotatingly mounted in bearings to a pivotally mounted lever arm 28b of the intermediate frame 29, said arm being loaded by a spring 28a so that the support wheel 24 is tightly pressed against its guide groove 22a, whereby a corresponding backing force develops between the other support wheels 23 and their respective guide groove 22b, thus achieving a reliable support and guidance of the wheels 23 and 24 against the support part 20. The support wheel 24 is arranged to operate as a drive wheel, which is pivotally mounted in bearings to a shaft 27 mounted on the lever arm 28b. The lower end of the shaft 27 is provided with a knurled knob 25, whose rotation allows the support part 20 to be rotated to various positions for the radiography of different transversal projections. Backed by the support part 20, the above described mechanism supports and always automatically aligns the skull of the patient P in a position in which the imaging projection is transversal, that is, at 90° angle to the tangential main direction of the dental arch. If any other cross-sectional projection of the dental arch different from the exactly orthogonal sectional projection at 90° angle is desired to be imaged, a fine-adjustment screw 26 is provided for minor adjustments of the imaging projection plane within certain limits.

Figure 8:
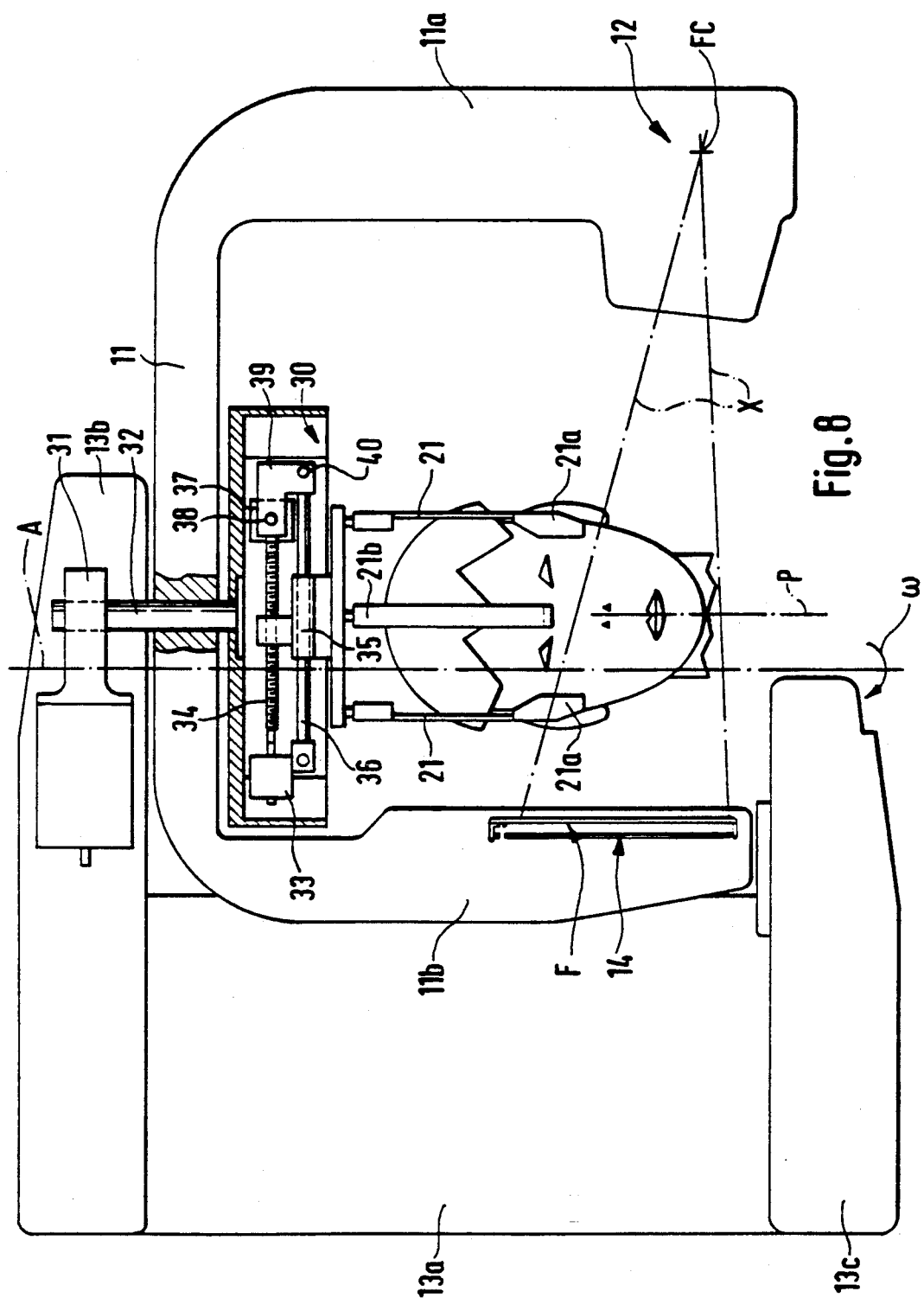
FIG. 8 shows in similar manner to that of FIGS. 1 and 3 such patient support elements which are located above the patient's head and fixed from above.

FIGS. 8, 9 and 10 show a support apparatus for the patient P, capable of supporting the patient's skull from above. Such an apparatus comprises a body part 30 which is supported by a central shaft 32 from a rotating motor actuator 31. The motor actuator 31 itself is fastened to a horizontal beam 13b of the body part. The body part 30 supports attached to it via an X-Y mechanism the support means of the patient that are mounted to a carriage 35 movable along a guide 36. The patient support means comprise both temporal support pads 21a mounted to the lower ends of vertical support members 21 and forehead support members 21b.

The attachment of patient support means illustrated in FIGS. 8 . . . 11 to the X-Y mechanisms is advantageously arranged so that the patient can be supported with the help of a single set of support elements in both the conventional panoramic imaging position (FIGS. 1 and 2) and the transversal projection imaging positions according the invention shown in FIGS. 8 and 9. Such an arrangement obviates the use of interchangeable support means. This kind of embodiment of the present invention is useful for new panoramic radiographic equipment which can thus be designed inherently suitable also for transversal projection radiography according to the invention.

In FIGS. 8 and 9 the patient is shown supported so that the radiographic image is taken on the film F in a transversal vertical plane P-P passing between the incisors. The X-Y mechanism adapted between the body part 30 and the carriage 35 comprises a X-directional transfer screw 34 connected to a motor 33 that moves the carriage 35 along the guide 36. The apparatus also has another transfer screw 38, which is connected to a motor 37 for the purpose of implementing transfer in the Y-direction. The transfer screw 38 rotated by the motor 37 is connected to a carriage 39 moving along a guide 40, said carriage further moving another carriage 35 in the Y-direction. In FIG. 10 the body part 30 is shown rotated to a position 30' by means of the motor actuator 31 and its shaft 32, whereby radiographic imaging takes place at the temporo-mandibular joint J₀ in the transversal vertical plane P-P.

Figure 11:
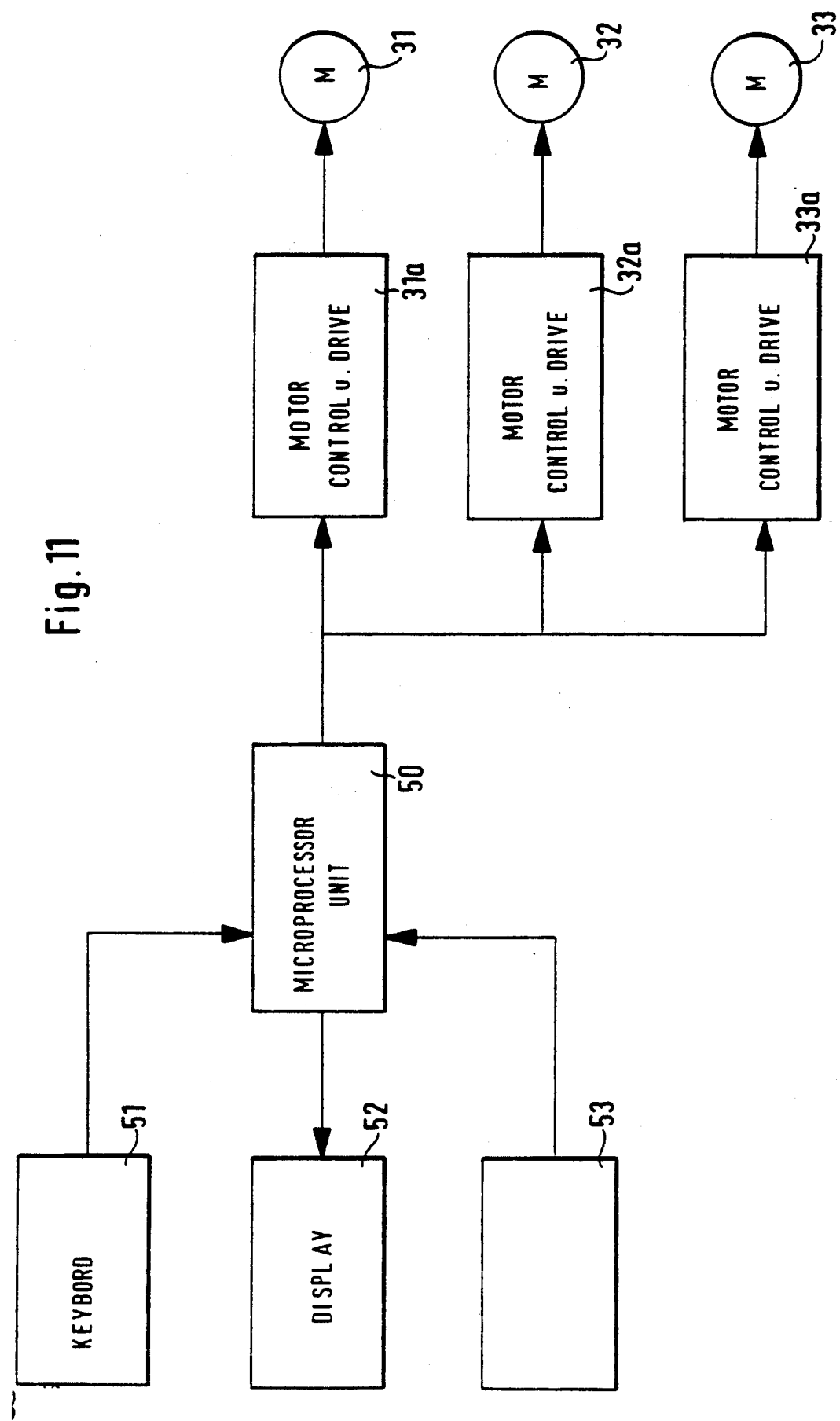
FIG. 11 shows a block diagram of an automatic control system for the apparatus illustrated in FIGS. 8, 9 and 10.

The X-Y and rotational mechanisms illustrated in FIGS. 8, 9 and 10 are driven by a control system shown in FIG. 11 comprising a keyboard 51 for entering the parameters that align the patient for a desired radiographic projection. The control system is comprised of a microprocessor unit 50, an attached display 52 and a digitizing tablet 53 suitable for transferring the imaging parameters to the system from, e.g., a radiographic image taken from the patient. The microprocessor unit 50 controls the function of the motors 31,32,33 via their control and driver units 31a,32a,33a so that the body part 30 of the patient positioning unit is rotated about the shaft 32 to the position required by radiographic projection and transferred with the X-Y mechanism driven by the motors 32 and 33 to such a position that is presumed by the radiographic parameters entered from the keyboard 52 or the digitizing tablet 52. The claims of the patent application are presented in the following, whereby the different details of the invention may be varied and deviated within the scope of the claims which define the invention from those of the exemplifying embodiments.

We claim:

1. In a method of narrow-beam tomography utilizing an x-ray source (12) whose narrow beam (X) is aimed to pass through a related object of a patient (P) to be radiographed and onto a movable (v₁) x-ray film (F), wherein the object to be radiographed from the patient is kept stationary in a certain position while the x-ray source and a film cassette (14) are rotated about a virtual axis of rotation (A-A), and wherein according to a first operating mode the patient (P) is supported by positioning means for exposing panoramic radiographic images of the dental arch so that the sharply plane (P-P) is located between the virtual axis of rotation (A-A) of the x-ray beam (X) and the film plane (F), the improvement for radiography of transversal projections of the dental arch (L) according to a second operating mode of the invention, comprising the steps of:

supporting the patient (P) in such a position that the virtual axis of rotation (A-A) of the x-ray beam (X) is located in the area between the sharply imaging plane (P-P) and the film plane (F), and the tissue layer in the sharply imaging plane (P-P) is located to the side of the x-ray source focus point (FC) with respect to the virtual axis of rotation (A-A); and moving the x-ray film (F) at a velocity (v1) determined by a predetermined imaging equation toward a direction which is opposite to the film motion velocity used in the first operating mode.

means controlling the motion of the x-ray film (14) to occur in a direction opposite to that of the conventional panoramic radiographic in which the imaging plane (P-P) is located in the area between the plane of the x-ray film (F) and the virtual axis of rotation (A-A).

2. A method as defined in claim 1, wherein the following imaging condition is fulfilled $$v_1/v_0 = L_1/L_0$$

where
$L_1$ = distance from the focus point (FC) to the film plane (F)
$L_0$ = distance from the focus point (FC) to the sharply imaging layer (P-P)

$$v_0 = \omega \cdot r$$

where
$\omega$ = angular velocity of rotational motion of the x-ray beam (X) about the virtual axis of rotation (A-A)
r = distance of imaged plane (P-P) from the virtual axis of rotation (A-A).

3. A method as defined in claim 1, comprising the step of locating the patient in the spaced between the x-ray source (12) and the film cassette (14) by positioning means, and transferring the positioning means to a position in which the patient is supported appropriately for transversal projection radiography of the teeth or areas nearby.

4. A method as defined in claim 3, comprising the step of transferring the patient support means by guidance elements (22a, 22b, 23, 24), whose shape substantially conforms to the shape of the dental arch (L).

5. A method as defined in claim 1, comprising the step of supporting the patient by means of support elements placed above the patient's skull, rotating said support elements about a vertical axis (32) attached to the body part (30) of the radiographic apparatus, and translating the patient support elements with the help of an X-Y mechanism (32 . . . 40) with respect to said rotatable body part (30) in order to align the object to be radiographed to a suitable position for the desired radiographic projection.

6. A method as defined in claim 1, comprising the step of supporting and locating the patient in the correct position in the first and second radiographic imaging modes by different sets of support elements that are detachable and reattachable to the panoramic radiographic apparatus in a mutually interchangeable manner.

7. A method as defined in claim 1, comprising the step of supporting the patient in the first and second radiographic imaging modes by a single set of support elements (FIGS. 8 . . . 11) that are rotatable and transferable to such support positions that are appropriate for both of the radiographic imaging modes.

8. In a panoramic tomographic apparatus for dental radiography, the apparatus comprising a body part (13a, 13b, 13c, 18) to which is mounted in bearings a second body part (11) rotatable about an axis, the second body part carrying at one end an x-ray source (12) and carrying at the other end a film cassette (14) capable of housing an x-ray film (F), and the space between said x-ray source (20) and said film cassette (14) being able to accommodate the object to be radiographed from the patient (P), and the apparatus further comprising an actuator operative to rotate said rotatable body part (11) in a plane for exposing a panoramic radiographic image, the improvement comprising:

positioning means operative to support the patient (P) for the radiography of transversal projections at a position in which a sharply imaging plane (P-P) is located in the area between the focus point (FC) of the x-ray source (12) and a virtual axis of rotation (A-A) of the x-ray beam (X) emitted from the source, and means controlling the motion of the x-ray film (14) to occur in a direction opposite to that of the conventional panoramic radiography in which the imaging plane (P-P) is located in the area between the plane of the x-ray film (F) and the virtual axis of rotation (A-A).

9. An apparatus as defined in claim 8, wherein the patient support elements used during transversal projection radiography are selectively detachable, and to the panoramic apparatus attachable, auxiliary elements that fit into the space between the x-ray source (12) and the film cassette (14) to replace the conventional patient support elements (15, 16, 16a, 17) in such a manner that permits unobstructed orbiting of the body part (11, 11a, 11b) supporting the x-ray source (12) and the film cassette (14) about the head of the patient (P).

10. An apparatus as defined in claim 8, further comprising a single set of patient skull support elements (30 . . . 40) operative to support the patient (P) both in a position required in conventional panoramic radiography and in at least one position appropriate for radiographing one or more transversal projection images.

11. An apparatus as defined in claim 8, further comprising:

a support part (20) shaped essentially conforming to the dental arch;

said support part incorporating guide elements (22a, 22b) shaped conforming to the dental arch and having moving wheels (23, 24); and at least one (24) of said wheels being operative as a drive wheel, whose rotation by a driven element (25, 26) permits the alignment of the support part (20) with support elements (21, 21a) of the patient's head to such a position in which the patient (P) is supported appropriately for transversal projection radiography from a desired direction.

12. An apparatus as defined in claim 8, further comprising:

a body part (30) adapted above the patient's skull and being supported by a central shaft 32 from a stationary body part (13b) of the apparatus so as to be rotatable about a certain virtual axis of rotation and said body part (30) mounts an X-Y mechanism operative to move the patient head supporting elements (21, 21a, 21b) to such a position in which the patient can be radiographed in a desired manner of transversal projection radiography.

13. An apparatus as defined in claim 8, further comprising:

a control unit incorporating a microprocessor unit (50), elements (51,53) for entry of control data related to the alignment of patient position, and other possible patient data to the microprocessor unit (50); and drive motors (31,32,33) driven by driver and control units (31a, 32a, 33a) of said microprocessor unit (50), said motors operative to transfer the patient support elements to a selected position required by transversal projection radiography.

* * * * *